US012807911B2

(12) United States Patent
Ayuso et al.

(10) Patent No.: US 12,807,911 B2
(45) Date of Patent: Nov. 24, 2026

(54) MICROFLUIDIC DEVICE AND METHOD FOR GENERATING A SKIN CONSTRUCT

(71) Applicant: Wisconsin Alumni Research Foundation, Madison, WI (US)

(72) Inventors: Jose Ayuso, Madison, WI (US); Catherine Reed McBain, Madison, WI (US); Seth Zima, Madison, WI (US); Rithvik Turaga, Madison, WI (US); Vijayasaradhi Setaluri, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 526 days.

(21) Appl. No.: 18/374,415

(22) Filed: Sep. 28, 2023

(65) Prior Publication Data

US 2025/0109365 A1 Apr. 3, 2025

(51) Int. Cl.

*C12M 3/00* (2006.01)
*C12M 1/00* (2006.01)
*C12M 3/06* (2006.01)

(52) U.S. Cl.

CPC ............ *C12M 21/08* (2013.01); *C12M 23/16* (2013.01); *C12M 23/20* (2013.01); *C12M 23/40* (2013.01)

(58) Field of Classification Search

CPC .............................. C12M 25/14; C12M 21/08
See application file for complete search history.

(56) References Cited

U.S. PATENT DOCUMENTS

| | | | | |
|---|---|---|---|---|
| 11,248,203 | B2 | 2/2022 | Levner et al. | |
| 2009/0011455 | A1* | 1/2009 | Warren | G01N 33/5044 435/325 |
| 2013/0143230 | A1* | 6/2013 | Tolias | C12Q 1/025 435/7.1 |
| 2014/0057311 | A1* | 2/2014 | Kamm | G01N 33/5029 216/33 |
| 2018/0346859 | A1* | 12/2018 | Varone | C12N 5/0629 |
| 2019/0010463 | A1* | 1/2019 | Matheu | C12N 5/0671 |

(Continued)

OTHER PUBLICATIONS

Volpe, C. M. O., Villar-Delfino, P. H., dos Anjos, P. M. F. & Nogueira-Machado, J. A. Cellular death, reactive oxygen species (ROS) and diabetic complications. Cell Death. Dis. 9, 119 (2018).

(Continued)

*Primary Examiner* — Nathan A Bowers
(74) *Attorney, Agent, or Firm* — Boyle Fredrickson, S.C

(57) ABSTRACT

A device and method are provided for generating a skin construct. The device includes a body having a chamber formed therein. The second portion of the chamber is filled with a polymerizable material and the material is allowed to polymerize within the second portion of the chamber. A cell media is deposited in the first portion of the chamber and a first portion of the cell media forms a skin construct on the polymerized material. The third portion of the chamber is filled with a media which contacts the polymerized material. A second portion of the cell media is removed from the first portion of the chamber such that ambient air in the first portion of the chamber forms an interface with the skin construct. The body may be rotated so as to allow the skin construct to be formed on the polymerized material and to be imaged with an imaging device.

22 Claims, 5 Drawing Sheets

(56) References Cited

U.S. PATENT DOCUMENTS

| | | | | |
|---|---|---|---|---|
| 2019/0032021 A1 | 1/2019 | Ingber et al. | | |
| 2019/0177678 A1* | 6/2019 | Bigliardi | C12M 23/16 | |
| 2020/0269234 A1* | 8/2020 | Kujala | C12M 23/16 | |
| 2021/0380912 A1* | 12/2021 | Hannen | C12M 21/08 | |
| 2022/0403315 A1* | 12/2022 | Chien | C12N 5/0062 | |
| 2023/0193182 A1* | 6/2023 | Young | C12M 29/10 435/297.2 | |
| 2024/0368517 A1* | 11/2024 | Krauss | C12M 27/16 | |
| 2026/0002109 A1* | 1/2026 | Hinojosa | C12M 23/42 | |

OTHER PUBLICATIONS

Vandewauw, I., Owsianik, G. & Voets, T. Systematic and quantitative mRNA expression analysis of TRP channel genes at the single trigeminal and dorsal root ganglion level in mouse. BMC Neurosci. 14, 21 (2013).

Chuang, H. H. & Lin, S. Oxidative challenges sensitize the capsaicin receptor by covalent cysteine modification. Proc. Natl Acad. Sci. USA. 106, 20097-20102 (2009).

Zherebitskaya, E., Akude, E., Smith, D. R. & Fernyhough, P. Development of selective axonopathy in adult sensory neurons isolated from diabetic rats: Role of glucose-induced oxidative stress. Diabetes 58, 1356-1364 (2009).

Okano, J. et al. Hyperglycemia induces skin barrier dysfunctions with impairment of epidermal integrity in non-wounded skin of type 1 diabetic mice. PLoS ONE 11, e0166215 (2016).

Talagas, M., Lebonvallet, N., Berthod, F. & Misery, L. Lifting the veil on the keratinocyte contribution to cutaneous nociception. Protein Cell. 11, 239-250 (2020).

Stapleton S., Chopra A. & Chen C. S. Force measurement tools to explore cadherin mechanotransduction. Cell Comm. Adhesion. 3, 193-205, (2014).

Muller, Q. et al. Development of an innervated tissue-engineered skin with human sensory neurons and Schwann cells differentiated from iPS cells. Acta Biomater. 82, 93-101 (2018).

Zhang, X. Y., Guo, Z., Li, T. P. & Sun, T. Dietary capsaicin normalizes CGRP peptidergic DRG neurons in experimental diabetic peripheral neuropathy. Sci. Rep. 11, 1704 (2021).

Dekoninck, S. et al. Defining the design principles of skin epidermis postnatal growth. Cell 181, 604-620 e622 (2020).

Natsuga, K. Epidermal barriers. Cold Spring Harb. Perspect. Med. 4, a018218 (2014).

Boulais, N. & Misery, L. The epidermis: a sensory tissue. Eur. J. Dermatol. 18, 119-127 (2008).

Snider, W. D. & McMahon, S. B. Tackling pain at the source: new ideas about nociceptors. Neuron 20, 629-632 (1998).

Lumpkin, E. A. & Caterina, M. J. Mechanisms of sensory transduction in the skin. Nature 445, 858-865 (2007).

Usoskin, D. et al. Unbiased classification of sensory neuron types by large-scale single-cell RNA sequencing. Nat. Neurosci. 18, 145-153 (2015).

Li, C. L. et al. Somatosensory neuron types identified by highcoverage single-cell RNA-sequencing and functional heterogeneity. Cell Res. 26, 83-102 (2016).

Wendelschafer-Crabb, G., Kennedy, W. R. & Walk, D. Morphological features of nerves in skin biopsies. J. Neurol. Sci. 242, 15-21 (2006).

Le Pichon, C. E. & Chesler, A. T. The functional and anatomical dissection of somatosensory subpopulations using mouse genetics. Front. Neuroanat. 8, 21 (2014).

Oaklander, A. L. & Siegel, S. M. Cutaneous innervation: form and function. J. Am. Acad. Dermatol. 53, 1027-1037 (2005).

Zylka, M. J., Rice, F. L. & Anderson, D. J. Topographically distinct epidermal nociceptive circuits revealed by axonal tracers targeted to Mrgprd. Neuron 45, 17-25 (2005).

Sokabe, T., Fukumi-Tominaga, T., Yonemura, S., Mizuno, A. & Tominaga, M. The TRPV4 channel contributes to intercellular junction formation in keratinocytes. J. Biol. Chem. 285, 18749-18758 (2010).

Roggenkamp, D. et al. Epidermal nerve fibers modulate keratinocyte growth via neuropeptide signaling in an innervated skin model. J. Investig. Dermatol. 133, 1620-1628 (2013).

Sondersorg, A. C. et al. Chemosensory information processing between keratinocytes and trigeminal neurons. J. Biol. Chem. 289, 17529-17540 (2014).

Ulmann, L. et al. Trophic effects of keratinocytes on the axonal development of sensory neurons in a coculture model. Eur. J. Neurosci. 26, 113-125 (2007).

Kumamoto, J. I. et al. Coculture system of keratinocytes and dorsalroot-ganglion-derived cells for screening neurotrophic factors involved in guidance of neuronal axon growth in the skin. Exp. Dermatol. 23, 58-60 (2014).

Pereira, U. et al. Development of an in vitro coculture of primary sensitive pig neurons and keratinocytes for the study of cutaneous neurogenic inflammation. Exp. Dermatol. 19, 931-935 (2010).

Tsutsumi, M., Goto, M., Denda, S. & Denda, M. Morphological and functional differences in coculture system of keratinocytes and dorsal-root-ganglion-derived cells depending on time of seeding. Exp. Dermatol. 20, 464-467 (2011).

Risueño, I., Valencia, L., Jorcano, J. L. & Velasco, D. Skin-on-a-chip models: General overview and future perspectives. APL Bioeng. 5, 049901 (2021).

Martorina, F., Casale, C., Urciuolo, F., Netti, P. A. & Imparato, G. In vitro activation of the neuro-transduction mechanism in sensitive organotypic human skin model. Biomaterials 113, 217-229 (2017).

Gall-Ianotto, C. L., Andres, E., Hurtado, S. P., Pereira, U. & Misery, L. Characterization of the first coculture between human primary keratinocytes and the dorsal root ganglion-derived neuronal cell line F-11. Neuroscience 210, 47-57 (2012).

Moreci, R. S. & Lechler, T. Epidermal structure and differentiation. Curr. Biol. 30, R144-R149 (2020).

Mori, N., Morimoto, Y. & Takeuchi, S. Skin integrated with perfusable vascular channels on a chip. Biomaterials 116, 48-56 (2017).

Abaci, H. E., Gledhill, K., Guo, Z., Christiano, A. M. & Shuler, M. L. Pumpless microfluidic platform for drug testing on human skin equivalents. Lab. Chip 15, 882-888 (2015).

Wufuer, M. et al. Skin-on-a-chip model simulating inflammation, edema and drug-based treatment. Sci. Rep. 6, 37471 (2016).

Denda, M., Nakatani, M., Ikeyama, K., Tsutsumi, M. & Denda, S. Epidermal keratinocytes as the forefront of the sensory system. Exp. Dermatol. 16, 157-161 (2007).

Van Gele, M., Geusens, B., Brochez, L., Speeckaert, R. & Lambert, J. Three-dimensional skin models as tools for transdermal drug delivery: challenges and limitations. Expert Opin. Drug Deliv. 8, 705-720 (2011).

Groeber, F., Holeiter, M., Hampel, M., Hinderer, S. & Schenke-Layland, K. Skin tissue engineering-in vivo and in vitro applications. Adv. Drug Deliv. Rev. 63, 352-366 (2011).

MacNeil, S. Progress and opportunities for tissue-engineered skin. Nature 445, 874-880 (2007).

Flaten, G. E. et al. In vitro skin models as a tool in optimization of drug formulation. Eur. J. Pharm. Sci. 75, 10-2 (2015).

Poumay, Y. et al. A simple reconstructed human epidermis: preparation of the culture model and utilization in in vitro studies. Arch. Dermatol. Res. 296, 203-211 (2004).

Shin, Y. et al. Microfluidic assay for simultaneous culture of multiple cell types on surfaces or within hydrogels. Nat. Protoc. 7, 1247-1259 (2012).

Roggenkamp, D. et al. Atopic keratinocytes induce increased neurite outgrowth in a coculture model of porcine dorsal root ganglia neurons and human skin cells. J. Investig. Dermatol. 132, 1892-1900 (2012).

Varga-Medveczky, Z., Kocsis, D., Naszlady, M. B., Fónagy, K. & Erdö, F. Skin-on-a-chip technology for testing transdermal drug delivery -starting points and recent developments. Pharmaceutics 13, 1852 (2021).

Blais, M. et al. Sensory neurons accelerate skin reepithelialization via substance P in an innervated tissue-engineered wound healing model. Tissue Eng. Part A. 20, 2180-2188 (2014).

(56) References Cited

OTHER PUBLICATIONS

Tracy, L. E., Minasian, R. A. & Caterson, E. J. Extracellular matrix and dermal fibroblast function in the healing wound. Adv. Wound Care 5, 119-136 (2016).
Bernstam, L., Vaughan, F. & Bernstein, I. Keratinocytes grown at the air-liquid interface. Vitr. Cell Dev. Biol. 22, 695-705 (1986).
Frankart, A. et al. Epidermal morphogenesis during progressive in vitro 3D reconstruction at the air-liquid interface. Exp. Dermatol. 21, 871-875 (2012).
Willits, R. K. & Skornia, S. L. Effect of collagen gel stiffness on neurite extension. J. Biomater. Sci. Polym. Ed. 15, 1521-1531 (2004).
Swindle-Reilly, K. E. et al. The impact of laminin on 3D neurite extension in collagen gels. J. Neural Eng. 9, 046007 (2012).
Roig-Rosello, E. & Rousselle, P. The human epidermal basement membrane: a shaped and cell instructive platform that aging slowly alters. Biomol. MDPI 10, 1607 (2020).
Na, K., Lee, M., Shin, H. W. & Chung, S. In vitro nasal mucosa glandlike structure formation on a chip. Lab. Chip 17, 1578-1584 (2017).
Schartner, E. et al. High glucose concentration suppresses a SIRT2 regulated pathway that enhances neurite outgrowth in cultured adult sensory neurons. Exp. Neurol. 309, 134-147 (2018).
Nozumi, M., Togano, T., Takahashi-Niki, K. & Igarashi, M. Identification of functional marker proteins in the mammalian growth cone. PNAS 106, 17211-17216 (2009).
Ramer, L. M., van Stolk, A. P., Inskip, J. A., Ramer, M. S. & Krassioukov, A. V. Plasticity of TRPV1-expressing sensory neurons mediating autonomic dysreflexia following spinal cord injury. Front. Physiol. 3, 257 (2012).
Ibrahim, Z. et al. Cutaneous collateral axonal sprouting reinnervates the skin component and restores sensation of denervated Swine osteomyocutaneous alloflaps. PLoS ONE 8, e77646 (2013).
Inoue, K. et al. Functional vanilloid receptors in cultured normal human epidermal keratinocytes. Biochem. Biophys. Res. Commun. 291, 124-129 (2002).
Van Acker, K. et al. Prevalence and impact on quality of life of peripheral neuropathy with or without neuropathic pain in type 1 and type 2 diabetic patients attending hospital outpatients clinics. Diabetes Metab. 35, 206-213 (2009).
Premkumar, L. S. & Pabbidi, R. M. Diabetic peripheral neuropathy: Role of reactive oxygen and nitrogen species. Cell Biochem. Biophys. 67, 373-383 (2013).
Lam, D. et al. RAGE-dependent potentiation of TRPV1 currents in sensory neurons exposed to high glucose. PLoS ONE 13, e0193312 (2018).

* cited by examiner

MICROFLUIDIC DEVICE AND METHOD FOR GENERATING A SKIN CONSTRUCT

REFERENCE TO GOVERNMENT GRANT

This invention was made with government support under W81XWH-19-1-0478 awarded by the ARMY/MRDC and under AR066524 awarded by the National Institutes of Health. The government has certain rights in the invention.

FIELD OF THE INVENTION

This invention relates generally to microfluidic devices, and in particular, to a microfluidic device and method for generating a skin construct.

BACKGROUND AND SUMMARY OF THE INVENTION

Research into new therapies for skin diseases is challenging for a number of reasons. As is known, skin cells are exposed to both atmospheric air and liquids within the body. However, conventional cell culture models do not accurately mimic the in vivo conditions necessary for insuring the reliability, validity, and transferability of the research. As such, dermatology and pulmonary researchers have turned to air-liquid interface systems to allow the researchers to more accurately mimic in vivo conditions.

Typically, an air-liquid interface system utilizes a transwell plate having inserts positioned in each well. The insert divides each well in upper and lower compartments, which are separated by a porous filter support. The lower compartment is filled with a liquid media and cells are cultured on porous filter support. It can be appreciated that one side of the cell culture is continuously exposed to the liquid media in the second compartment, while the opposite side of the cell culture is surrounded by air. This arrangement, in turn, allows the researcher to produce a skin layer in an environment that more closely resembles in vivo conditions.

While functional for their intended purpose, these prior air-liquid interface systems have certain limitations. For example, air-liquid interface system utilizing transwell plates have a limited capacity for multiple assays due in part to the difficulty of extracting cells from them. Further, transwell plates are expensive to manufacture, the manufacturing process is slow, and the transwell plates do not allow for easy imaging in 3-dimensions. Consequently, there exists a need to provide an air-liquid interface system for generating optically transparent skin that is simple and inexpensive to manufacture and allows for easy 3-dimensional imaging.

Therefore, it is primary object and feature of the present invention to provide a microfluidic device and method for generating a skin construct.

It is a further object and feature of the present invention to provide a microfluidic device and method for generating a skin construct in an environment that more closely resembles in vivo conditions.

It is a still further object and feature of the present invention to provide a microfluidic device and method for generating a skin construct that is simple and inexpensive to manufacture and allows for easy 3-dimensional imaging.

In accordance with the present invention, a device is provided for generating a skin construct. The device includes a body having a chamber formed therein. The chamber is defined by opposing first and second surfaces interconnected and spaced by an inner surface. The chamber includes a first portion adapted for receiving a cell culture therein, a second portion adapted for receiving a polymerizable material therein and a third portion adapted for receiving a media therein. A first flow restriction projects from the inner surface between the first and second portions of the chamber. The first flow restriction is configured to discourage flow of polymerizable material from the second portion of the chamber to the first portion of the chamber. A second flow restriction projects from the inner surface between the second and third portions of the chamber. The second flow restriction is configured to discourage flow of polymerizable material from the second portion of the chamber to the third portion of the chamber. A cell port extends through the first surface and communicates with the first portion of the chamber. A material port extends through the first surface and communicates with the second portion of the chamber. A media port extends through the first surface and communicates with the third portion of the chamber. The first, second and third portions of the chamber have corresponding lengths. The length of the second portion of the chamber is less than the length of the first portion of the chamber. Similarly, the length of the second portion of the chamber is less than the length of the third portion of the chamber.

The first flow restriction is defined by first and second projections extending from the inner surface towards each other and being spaced by a length. The length between the first and second projections is less than the length of the second chamber. Similarly, the second flow restriction is defined by first and second projections extending from the inner surface towards each other and being spaced by a length. The length between the first and second projections of the second flow restriction is less than the length of the second chamber.

The first, second and third portions of the chamber also have corresponding widths. The width of the second portion of the chamber is greater than the width of the first portion of the chamber. In addition, the width of the second portion of the chamber is greater than the width of the third portion of the chamber.

In accordance with a further aspect of the present invention, a method is provided for generating a skin construct. The method includes the step of providing a chamber in a body. The chamber has first, second and third portions. The second portion of the chamber is filed with a polymerizable material and the material is allowed to polymerize within the second portion of the chamber. A cell media is deposited in the first portion of the chamber. A first portion of the cell media forms a skin construct on the polymerized material. The third portion of the chamber is filed with a media. The media contacts the polymerized material.

A second portion of the cell media is removed from the first portion of the chamber such that ambient air in the first portion of the chamber forms an interface with the skin construct. A flow of polymerizable material into the first portion of the chamber as the second chamber is filled with the polymerizable material is discouraged and a flow of polymerizable material into the third portion of the chamber as the second chamber is filled with the polymerizable material is discouraged.

In accordance with a still further aspect of the present invention, a method is provided for generating and imaging a skin construct. The method includes the step of providing a chamber in a body. The chamber is defined between a first wall and a second wall, and has first, second and third portions. The body is orientated such that the second wall lies in a generally horizontal plane. The second portion of the chamber is filled with a polymerizable material and the material is allowed to polymerize within the second portion of the chamber. A cell media is deposited in the first portion of the chamber and the body is rotated such that the first and second wall lie in generally vertical planes. A first portion of the cell media forms a skin construct on the polymerized material. The third portion of the chamber is filled with a media. The media contacts the polymerized material. A second portion of the cell media is removed from the first portion of the chamber such that ambient air in the first portion of the chamber forms an interface with the skin construct. The skin construct is imaged with an imaging device.

The body includes a cell port extending through the first wall and communicating with the first portion of the chamber. A material port extends through the first surface and communicates with the second portion of the chamber. A media port extends through the first surface and communicates with the third portion of the chamber. It is contemplated to discourage a flow of polymerizable material in the first portion of the chamber as the second chamber is filled with the polymerizable material and to discourage a flow of polymerizable material in the third portion of the chamber as the second chamber is filled with the polymerizable material. More specifically, the body may include at least one projection extending into chamber. The at least one projection discourages the flow of polymerizable material into the first portion of the chamber as the second chamber is filled with the polymerizable material. In addition, the at least one projection discourages the flow of polymerizable material into the third portion of the chamber as the second chamber is filed with the polymerizable material.

The first, second and third portions of the chamber have corresponding lengths. The length of the second portion of the chamber is less than the length of the first portion of the chamber. Similarly, the length of the second portion of the chamber is less than the length of the third portion of the chamber. In addition, the first, second and third portions of the chamber have corresponding widths. The width of the second portion of the chamber is greater than the width of the first portion of the chamber and the width of the second portion of the chamber is greater than the width of the third portion of the chamber.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings.

DETAILED DESCRIPTION OF THE DRAWINGS

Figure 1:
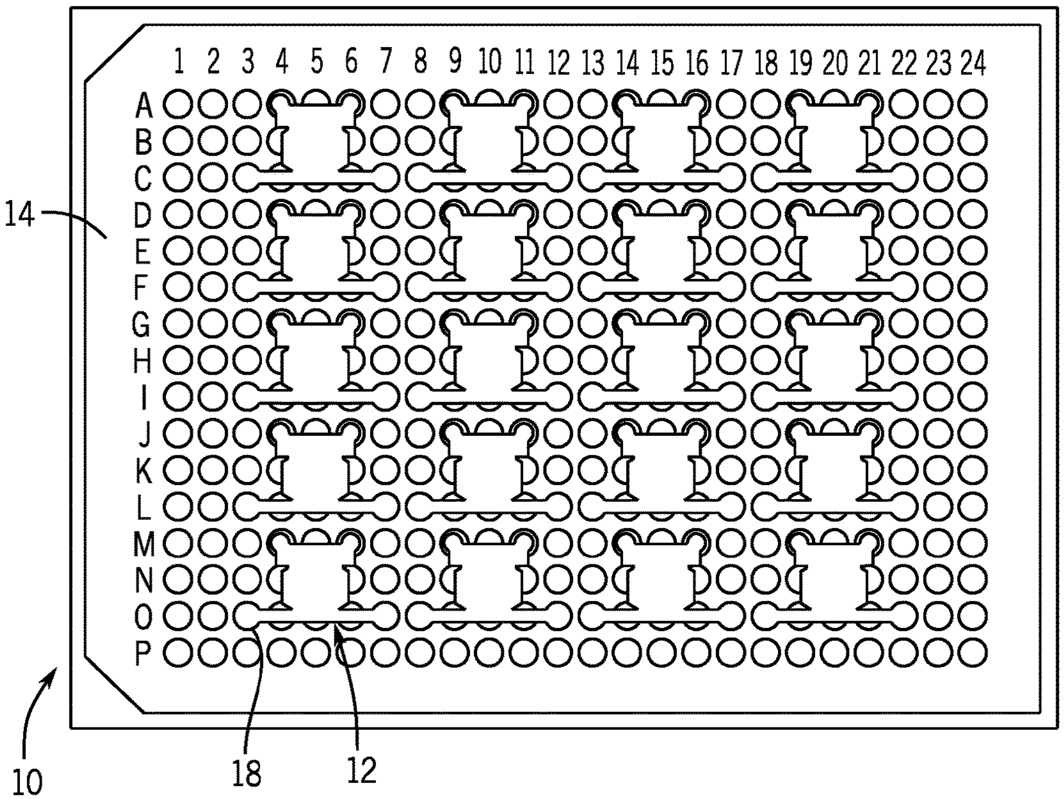
FIG. 1 is a top plan view of well plate including a microfluidic device in accordance with the present invention.

Referring to FIG. 1, a well plate adapted for receiving a plurality of microfluidic devices for generating a skin construct is generally designated by the reference numeral 10. It is contemplated for well-plate 10 to include a predetermined number of microfluidic devices 12 formed in outer surface 14 thereof. In the depicted embodiment, well plate 10 includes twenty (20) microfluidic devices arranged in rows and columns, however, microfluidic devices 12 in well plate 10 may be arrange in a different configurations and the well plate 10 may include any number of microfluidic devices 12 therein without deviating from the scope of the present invention. As hereinafter described, microfluidic devices 12 are identical in structure, and as such, the description of microfluidic device 12 hereinafter provided is intended to fully describe each of the microfluidic devices 12 formed in well plate 10, as if fully described herein.

Figure 2:
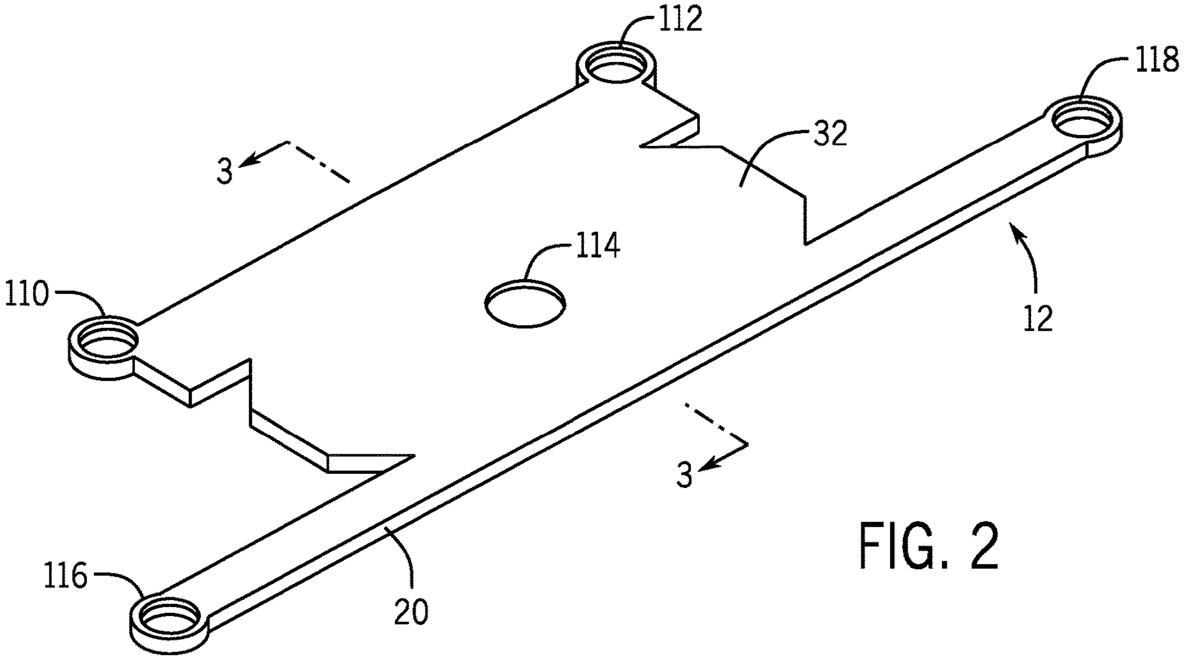
FIG. 2 is an isometric view of a microfluidic device in accordance with the present invention.
Figure 3:
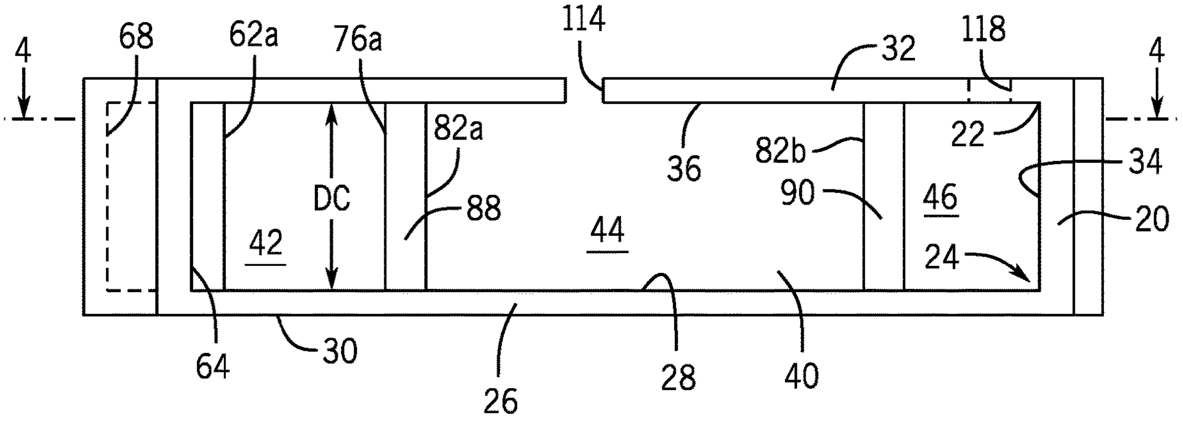
FIG. 3 is a cross-sectional view of the microfluidic device of the present invention taken along line 3-3 of FIG. 2.
Figure 4:
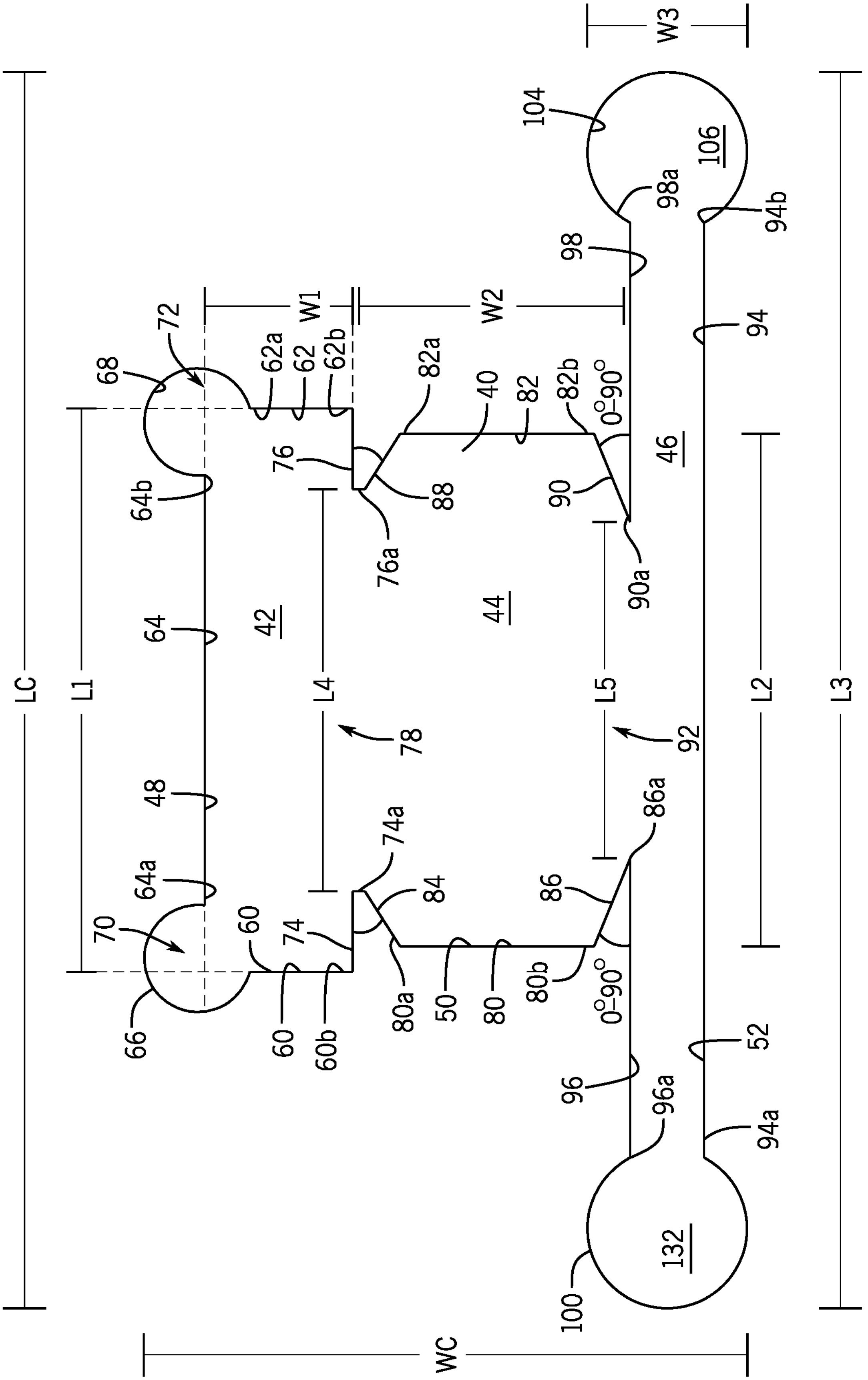
FIG. 4 is a cross-sectional view of the microfluidic device of the present invention taken along line 4-4 of FIG. 3.

It is contemplated for microfluidic devices 12 to be fabricated within well plate 10 or may be fabricated individually and deposited within a corresponding well 18 in outer surface 14 of well plate 10. Referring to FIGS. 2-4, each microfluidic device 12 is defined by outer wall 20 having upper and lower ends 22 and 24, respectively. Outer wall 20 may be of uniform thickness or have varying thicknesses without deviating from the scope of the present invention. Lower end 24 of outer wall 20 of microfluidic device 12 is closed by end wall 26 having inner and outer surfaces 28 and 30, respectively. It is contemplated for end wall 26 to be removably connected to lower end 24 of outer wall 20 of microfluidic device 12 to facilitate access to the interior of microfluidic device 12.

Access wall 32 extends radially inward from inner surface 34 of outer wall 20 adjacent upper end 22 thereof and lies in a place generally parallel to end wall 26. Inner surface 36 of access wall 32, inner surface 28 of end wall 26, and inner surface 34 of outer wall 20 define chamber 40 therebetween. As hereinafter described, chamber 40 is defined by first portion 42 adapted for receiving a cell culture therein, second portion 44 adapted for receiving a polymerizable material, e.g. a hydrogel, therein and third portion 46 adapted for receiving a media, e.g. a growth media or nutrients, therein. As best seen in FIG. 4, first portion 42 of chamber 40 is defined by corresponding first portion 48 of inner surface 34 of outer wall 20, second portion 44 of chamber 40 is defined by corresponding second portion 50 of inner surface 34 of outer wall 20, and third portion 46 of chamber 40 is defined by corresponding third portion 52 of inner surface 34 of outer wall 20.

Referring to FIGS. 3-4, chamber 40 has a depth DC in the range of 0.1 millimeters (mm) to 1 mm; an overall length LC, preferably, in the range of 5 mm to 20 mm; and an overall width WC, preferably, in the range 1.2 mm to 5 mm. Depth DC of chamber 40 ensures the skin construct to be formed, FIGS. 5F and 6, has adequate surface area to provide an air-liquid interface, as hereinafter described. First, second and third portions 42, 44 and 46, respectively, of chamber 40 have corresponding lengths L1, L2 and L3, respectively, and corresponding widths W1, W2 and W3, respectively. Preferably, length L2 of second portion 44 of chamber 40 is less than length L1 of first portion 42 of chamber 40 and length L2 of second portion 44 of chamber 40 is less than length L3 of third portion 46 of chamber 40. By way of example, length L1 of first portion 42 of chamber 40 is in the range of 2 mm to 15 mm; length L2 of second portion 44 of chamber 40 is in the range of 2 mm to 10 mm; and length L3 of third portion 46 of chamber 40 is in the range of 5 mm to 20 mm. Lengths L1, L2 and L3 of first, second and third portions 42, 44 and 46, respectively, of chamber 40 are broadly selected to recapitulate physiology of human skin, as hereinafter described.

It is contemplated for width W2 of second portion 44 of chamber 40 is greater than width W1 of first portion 42 of chamber 40 and width W2 of second portion 44 of chamber 40 is less than width W3 of third portion 46 of chamber 40. By way of example, width W1 of first portion 42 of chamber 40 is in the range of 0.25 mm to 2 mm; width W2 of second portion 44 of chamber 40 is in the range of 0.6 mm to 3 mm; and width W3 of third portion 46 of chamber 40 is in the range of 0.25 mm to 2 mm. Widths W1, W2 and W3 of first, second and third portions 42, 44 and 46, respectively, of chamber 40 are selected to maximize surface area for cell adherence and nutrient diffusion, as hereinafter described.

First portion 48 of inner surface 34 of outer wall 20 includes opposing, first and second end faces 60 and 62, respectively, which are generally parallel. First end face 60 extends between first and second terminal edges 60*a* and 60*b*, respectively. Similarly, second end face 62 extends between first and second terminal edges 62*a* and 62*b*, respectively. Side face 64 is generally perpendicular to first and second end faces 60 and 62, respectively, and terminates at first and second terminal edges 64*a* and 64*b*, respectively. First arcuate face 66 extends between first terminal edge 60*a* of first end face 60 and first terminal edge 64*a* of side face 64 so as to define cell port 70 of first portion 42 of chamber 40. Second arcuate face 68 extends between first terminal edge 62*a* of second end face 62 and second terminal edge 64*b* of side face 64 so as to define cell port 72 of first portion 42 of chamber 40.

First portion 48 of inner surface 34 of outer wall 20 further includes first and second restriction faces 74 and 76, respectively, which lie in a common plane generally parallel to and spaced from side face 64. More specifically, first restriction face 74 projects from second terminal edge 60*b* of first end face 60 and second restriction face 76 projects from second terminal edge 62*b* of second end face 62. Terminal edges 74*a* and 76*a* of first and second restriction faces 74 and 76, respectively, define an opening 78 between first and second portions 42 and 44, respectively, of chamber 40 so as to allow communication therebetween. Opening 78 has a length L4 less than length L2 of second portion 44 of chamber 40, and preferably, in the range of 2 mm to 15 mm, such that first and second restriction faces 74 and 76, respectively, act as pinning features to ensure polymerizable material received in second portion 44 of chamber 40 is constrained therein and does not invade first portion 42 of chamber 40, as hereinafter described.

Second portion 50 of inner surface 34 of outer wall 20 includes opposing, first and second end faces 80 and 82, respectively, which are generally parallel to each other. First end face 80 extends between first and second terminal edges 80*a* and 80*b*, respectively. Similarly, second end face 82 extends between first and second terminal edges 82*a* and 82*b*, respectively. Angular faces 84 and 86, respectively, project from corresponding first and second terminal edges 80*a* and 80*b*, respectively, of first end face 80 and diverge from each other. Angular face 84 terminates at and intersects terminal edge 74*a* of first restriction face 74. It can be understood that angular face 84 and first restriction face 74 define an acute angle therebetween. Angular face 86 terminates at terminal edge 86*a*.

Angular faces 88 and 90, respectively, project from corresponding first and second terminal edges 82*a* and 82*b*, respectively, of second end face 82 and diverge from each other. Angular face 88 terminates at terminal edge 76*a* of second restriction face 76. It can be understood that angular face 88 and second restriction face 76 define an acute angle therebetween. Angular face 90 terminates at terminal edge 90*a*. Terminal edges 88*a* and 90*a* of angular faces 88 and 90, respectively, define an opening 92 between second and third portions 44 and 46, respectively, of chamber 40 so as to allow communication therebetween.

Third portion 52 of inner surface 34 of outer wall 20 includes side face 94 which is generally parallel to side face 64 and terminates at first and second terminal edges 94*a* and 94*b*, respectively. Third portion 52 of inner surface 34 of outer wall 20 further includes first and second restriction faces 96 and 98, respectively, which lie in a common plane and generally parallel to and spaced from side face 94. More specifically, first restriction face 96 projects from terminal edge 88*a* of angular face 88 and terminates at terminal edge 96*a*. Second restriction face 98 projects from terminal edge 90*a* of angular face 90 and terminal edge 98*a*. Opening 92 has a length L5 less than length L3 of third portion 46 of chamber 40, and preferably, in the range of 2 mm to 15 mm, such that first and second restriction faces 96 and 98, respectively, act as pinning features to ensure polymerizable material received in second portion 44 of chamber 40 is constrained therein and does not invade third portion 46 of chamber 40.

First arcuate face 100 extends between first terminal edge 94*a* of side face 94 and terminal edge 96*a* of first restriction face 96 so as to define media port 102 of third portion 46 of chamber 40. Second arcuate face 104 extends between second terminal edge 94*b* of side face 94 and terminal edge 98*a* of second restriction face 98 so as to define media port 106 of third portion 46 of chamber 40.

Referring to FIG. 2, access wall 32 includes apertures 110 and 112, respectively, which are axially aligned with and communicate with corresponding first and second cell ports 70 and 72, respectively, of first portion 42 of chamber 40. Media port or aperture 114 extends through access wall 32 and communicates with second portion 44 of chamber 40. Apertures 116 and 118, respectively, which are axially aligned with and communicate with corresponding media ports 102 and 106, respectively, of third portion 46 of chamber 40. It is contemplated for apertures 110, 112, 114, 116, and 118 to have diameters in the range of 0.1 mm to 2 mm to ensure ease of loading of first, second, and third portions 42, 44 and 46, respectively, of chamber 40, as hereinafter described.

Figures 5A, 5B, 5C, 5D, 5E, 5F:
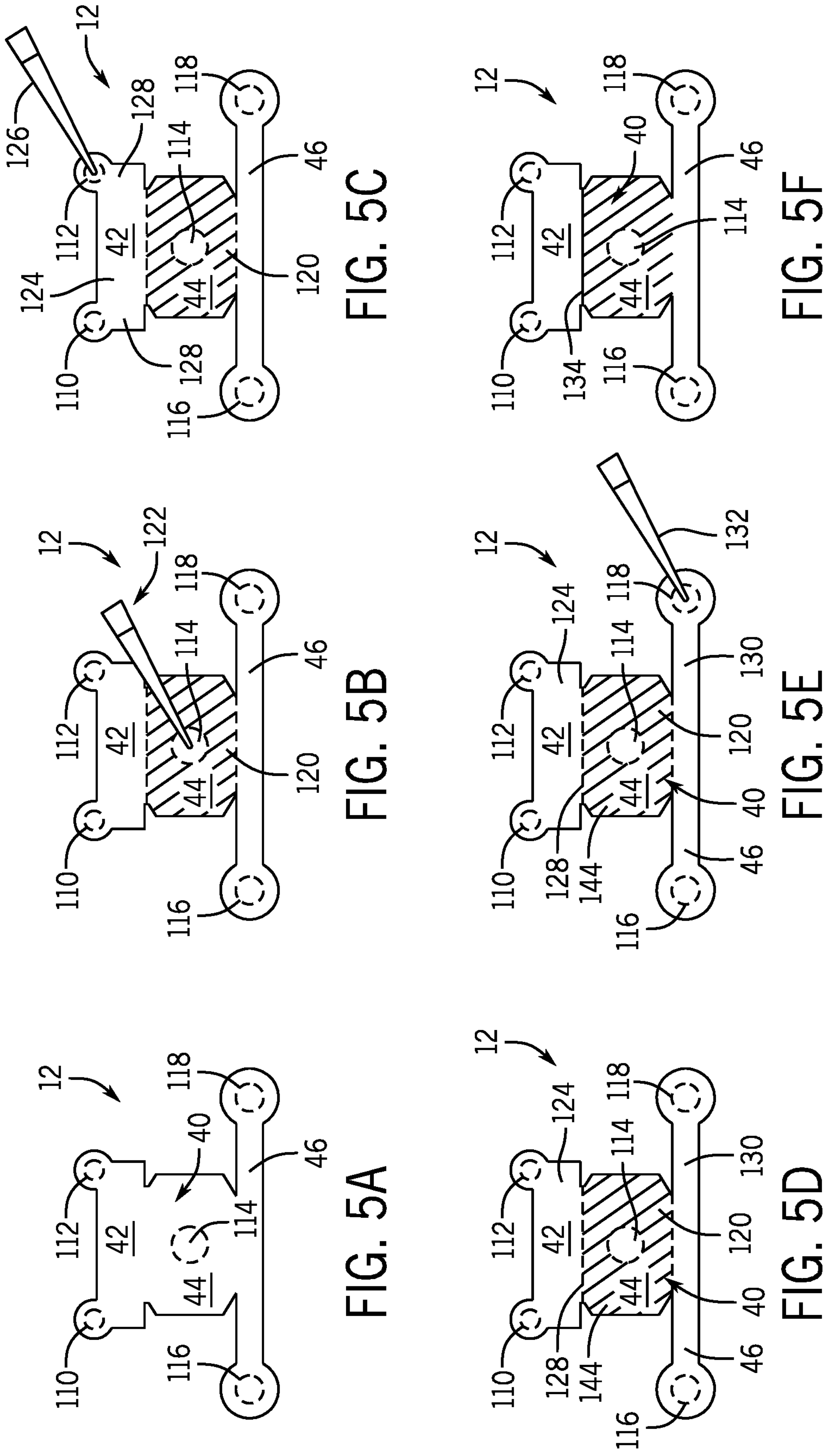
FIG. 5A is a cross-sectional view, similar to FIG. 4, showing an initial step for effectuating the methodology of the present invention.
FIG. 5B is a cross-sectional view of the microfluidic device, similar to FIG. 5A, showing a subsequent step for effectuating the methodology of the present invention.
FIG. 5C is a cross-sectional view of the microfluidic device, similar to FIG. 5B, showing a further step for effectuating the methodology of the present invention.
FIG. 5D is a cross-sectional view of the microfluidic device, similar to FIG. 5C, showing a still further step for effectuating the methodology of the present invention.
FIG. 5E is a cross-sectional view of the microfluidic device, similar to FIG. 5D, showing a still further step for effectuating the methodology of the present invention.
FIG. 5F is a cross-sectional view of the microfluidic device, similar to FIG. 5E, showing a still further step for effectuating the methodology of the present invention.
Figure 6:
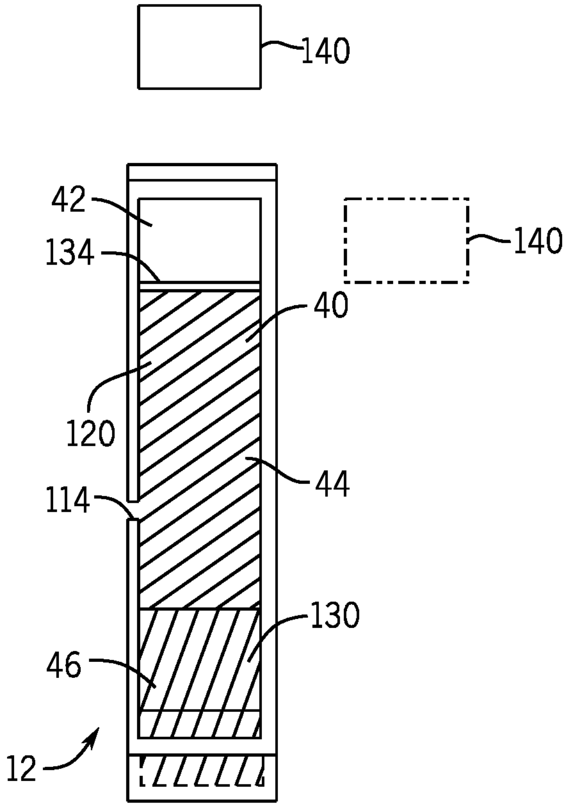
FIG. 6 is a cross-sectional view of the microfluidic device of the present invention, similar to FIG. 3, showing a skin construct fabricated in the microfluidic device.

Referring to FIGS. 5A-5F, in operation, microfluidic device 12 (or well-plate 10 housing microfluidic device 12) is positioned such that end wall 26 is lies in a generally horizontal plane, FIG. 5A. Polymerizable material 120 is loaded into second portion 44 of chamber 40 through aperture 114 in access wall 32 in any conventional matter, for example, using pipette 122, FIG. 5B. As noted above, first and second restriction faces 74 and 76, respectively, act as pinning features to ensure polymerizable material 120 received in second portion 44 of chamber 40 is constrained therein and does not invade first portion 42 of chamber 40. Similarly, first and second restriction faces 96 and 98, respectively, act as pinning features to ensure polymerizable material 20 received in second portion 44 of chamber 40 is constrained therein and does not invade third portion 46 of chamber 40.

After a time period, e.g. fifteen (15) minutes, polymerizable material 120 received in second portion 44 of chamber 40 polymerizes. Once polymerizable material 120 received in second portion 44 of chamber 40 is polymerized, cell culture 124 is loaded into first portion 42 of chamber 40 at least one of apertures 110 and 112, respectively, (e.g., aperture 112) through access wall 32, in any conventional matter, for example, using pipette 126, FIG. 5C. Once cell culture 124 is loaded into first portion 42 of chamber 40, microfluidic device 12 is rotated 90 degrees such that end wall 26 of microfluidic device 12 is lies in a generally vertical plane, FIG. 5D. It can be appreciated that cell culture 124 contacts polymerized material 120 through opening 78 between first and second portions 42 and 44, respectively, of chamber 40. Cells 128 in cell culture 124 are allowed to settle and adhere to polymerizable material 120.

As cells 128 in cell culture 124 settle and adhere to polymerizable material 120, media 130 is loaded into third portion 46 of chamber 40 through at least one of apertures 116 and 118, respectively, in access wall 32, in any conventional matter, for example, using pipette 132, FIG. 5E. With media 130 in third portion 46 of chamber 40, It can be appreciated understood that media 130 in third portion 46 of chamber 40 contacts polymerized material 120 in second portion 44 of chamber 40 through opening 92 between second and third portions 44 and 46, respectively, of chamber 40. Media 130 then permeates polymerized material 120, for reasons hereinafter described.

Once cells 128 in cell culture 124 settle and adhere to polymerized material 120, a layer or skin construct 134 of cells 128 is formed along the intersection of cell culture 124 and polymerizable material 120. Thereafter, cell culture 124 in first portion 42 of chamber 40 is removed therefrom, e.g. using a vacuum or the like, thereby establishing an air interface between skin construct 134 and the environment within first portion 42 of chamber 40. Similarly, media 130 permeating polymerized material 120 communicates with skin construct 134 through opening 78 between first and second portions 42 and 44, respectively, of chamber 40, thereby forming a liquid interface between skin construct 134 and media 130 permeating polymerized material 120 in second portion 44 of chamber 40.

As described, it can be appreciated that one side of skin construct 134 is continuously exposed to media in the second portion of 44 of chamber 40, while the opposite side of skin construct 134 is surrounded by air. This arrangement, in turn, provides a researcher with an environment for skin construct 134 that more closely resembles in vivo conditions. Thereafter, image device 140 may be used to image skin construct 134 from various locations to allow a user to consider the effects of the media on skin construct 134.

Various modes of carrying out the invention are contemplated as being within the scope of the following claims particularly pointing out and distinctly claiming the subject matter that is regarded as the invention.

We claim:

1. A device for generating a skin construct, comprising a body including:

a chamber formed therein and being defined by opposing first and second surfaces interconnected and spaced by an inner surface, the chamber including a first portion adapted for receiving a cell culture therein, a second portion adapted for receiving a polymerizable material therein and a third portion adapted for receiving a media therein, the first, second and third portions of the chamber having corresponding lengths;

a first flow restriction projecting from the inner surface between the first and second portions of the chamber, the first flow restriction:

defined by first and second projections extending from the inner surface towards each other and being spaced by a length, the length between the first and second projections being less than the length of the second portion of the chamber;

the first projection including a restriction face directed toward and partially defining the first portion of the chamber;

the second projection including a restriction face directed toward and partially defining the first portion of the chamber; and the first and second projections configured to discourage flow of polymerizable material from the second portion of the chamber to the first portion of the chamber; and a second flow restriction projecting from the inner surface between the second and third portions of the chamber, the second flow restriction:

defined by first and second projections extending from the inner surface towards each other and being spaced by a length, the length between the first and second projections of the second flow restriction being less than the length of the second portion of the chamber;

the first projection of the second flow restriction including a restriction face directed toward and partially defining the third portion of the chamber;

the second projection of the second flow restriction including a restriction face directed toward and partially defining the third portion of the chamber, and the first and second projections of the second flow restriction configured to discourage flow of polymerizable material from the second portion of the chamber to the third portion of the chamber.

2. The device of claim 1 further comprising a cell port extending through the first surface and communicating with the first portion of the chamber.

3. The device of claim 1 further comprising a material port extending through the first surface and communicating with the second portion of the chamber.

4. The device of claim 1 further comprising a media port extending through the first surface and communicating with the third portion of the chamber.

5. The device of claim 1 wherein the length of the second portion of the chamber being less than the length of the first portion of the chamber.

6. The device of claim 1 wherein the length of the second portion of the chamber being less than the length of the third portion of the chamber.

7. The device of claim 1 wherein the first, second and third portions of the chamber have corresponding widths, the width of the second portion of the chamber being greater than the width of the first portion of the chamber.

8. The device of claim 1 wherein the first, second and third portions of the chamber have corresponding widths, the width of the second portion of the chamber being greater than the width of the third portion of the chamber.

9. A method for generating and imaging a skin construct, comprising the steps of:

providing a chamber in a body, the chamber defined between a first wall and a second wall and having first, second and third portions;

orientating the body such that the second wall lies in a generally horizontal plane;

filing the second portion of the chamber with a polymerizable material and allowing the material to polymerize within the second portion of the chamber;

depositing a cell media in the first portion of the chamber;

rotating the body such that the first and second walls lie in generally vertical planes whereby a first portion of the cell media forming a skin construct on the polymerized material; and filling the third portion of the chamber with a media, the media contacting the polymerized material; and imaging the skin construct with an imaging device.

10. The method of claim 9 comprising the additional step of removing a second portion of the cell media from the first portion of the chamber such that ambient air in the first portion of the chamber forms an interface with the skin construct.

11. The method of claim 9 comprising the additional step of discouraging a flow of polymerizable material into the first portion of the chamber as the second chamber is filled with the polymerizable material.

12. The method of claim 11 comprising the additional step of discouraging a flow of polymerizable material into the third portion of the chamber as the second chamber is filled with the polymerizable material.

13. A method for generating and imaging a skin construct, comprising the steps of:

providing a chamber in a body, the chamber defined between a first wall and a second wall and having first, second and third portions;

orientating the body such that the second wall lies in a generally horizontal plane;

filing the second portion of the chamber with a polymerizable material and allowing the material to polymerize within the second portion of the chamber;

depositing a cell media in the first portion of the chamber and rotating the body such that the first and second wall lie in generally vertical planes whereby a first portion of the cell media forming a skin construct on the polymerized material;

filling the third portion of the chamber with a media, the media contacting the polymerized material;

removing a second portion of the cell media from the first portion of the chamber such that ambient air in the first portion of the chamber forms an interface with the skin construct; and imaging the skin construct with an imaging device.

14. The method of claim 13 wherein the body includes:

a cell port extending through the first wall and communicating with the first portion of the chamber;

a material port extending through the first surface and communicating with the second portion of the chamber; and a media port extending through the first surface and communicating with the third portion of the chamber.

15. The method of claim 3 comprising the additional step of discouraging a flow of polymerizable material in the first portion of the chamber as the second chamber is filled with the polymerizable material.

16. The method of claim 15 comprising the additional step of discouraging a flow of polymerizable material in the third portion of the chamber as the second chamber is filled with the polymerizable material.

17. The method of claim 13 wherein the first, second and third portions of the chamber have corresponding lengths, the length of the second portion of the chamber being less than the length of the first portion of the chamber.

18. The method of claim 13 wherein the first, second and third portions of the chamber have corresponding lengths, the length of the second portion of the chamber being less than the length of the third portion of the chamber.

19. The method of claim 13 wherein the body includes at least one projection extending into chamber, the at least one projection discouraging a flow of polymerizable material into the first portion of the chamber as the second chamber is filled with the polymerizable material.

20. The method of claim 13 wherein the body includes at least one projection extending into chamber, the at least one projection discouraging a flow of polymerizable material into the third portion of the chamber as the second chamber is filed with the polymerizable material.

21. The method of claim 13 wherein the first, second and third portions of the chamber have corresponding widths, the width of the second portion of the chamber being greater than the width of the first portion of the chamber.

22. The method of claim 13 wherein the first, second and third portions of the chamber have corresponding widths, the width of the second portion of the chamber being greater than the width of the third portion of the chamber.

* * * * *